(12) United States Patent
Wang et al.

(10) Patent No.: US 10,351,891 B2
(45) Date of Patent: Jul. 16, 2019

(54) HYDROXYACYL-COENZYME A DEHYDROGENASE GENE, AN ACYL-COENZYME A THIOLASE GENE, GENETICALLY ENGINEERED STRAINS AND A USE THEREOF

(71) Applicant: EAST CHINA UNIVERSITY OF SCIENCE AND TECHNOLOGY, Shanghai (CN)

(72) Inventors: Fengqing Wang, Shanghai (CN); Dongzhi Wei, Shanghai (CN); Liqin Xu, Shanghai (CN); Haohao Liu, Shanghai (CN); Xinbin Liu, Shanghai (CN); Nenghui Chen, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 0 days.

(21) Appl. No.: 15/535,274

(22) PCT Filed: Dec. 12, 2014

(86) PCT No.: PCT/CN2014/093667
§ 371 (c)(1),
(2) Date: Jun. 12, 2017

(87) PCT Pub. No.: WO2016/090622
PCT Pub. Date: Jun. 16, 2016

(65) Prior Publication Data
US 2018/0087082 A1 Mar. 29, 2018

(51) Int. Cl.
*C12P 33/02* (2006.01)
*C12P 33/00* (2006.01)
*C12N 9/10* (2006.01)
*C12N 9/04* (2006.01)
*C12R 1/32* (2006.01)

(52) U.S. Cl.
CPC ............ *C12P 33/02* (2013.01); *C12N 9/0006* (2013.01); *C12N 9/10* (2013.01); *C12N 9/1029* (2013.01); *C12P 33/00* (2013.01); *C12Y 101/01035* (2013.01); *C12Y 203/01009* (2013.01); *C12R 1/32* (2013.01)

(58) Field of Classification Search
None
See application file for complete search history.

(56) References Cited

PUBLICATIONS

Nesbitt et al. Infection and Immunity, vol. 78, No. 1, p. 275-282, Jan. 2010.*
Database PIR_80 accession No. C70677, Jul. 9, 2004.*
Pearson et al. Curr Protoc bioinformatics. 2013; doi:10.1002/0471250953.bi0301s42 pp. 1-9.*

* cited by examiner

*Primary Examiner* — Oluwatosin A Ogunbiyi
(74) *Attorney, Agent, or Firm* — Robert L. Stearns; Dickinson Wright PLLC (57) ABSTRACT

The present invention provides a hydroxyacyl-coenzyme A dehydrogenase gene, an acyl-coenzyme A thiolase gene, genetically engineered strains and a use thereof. The hydroxyacyl-coenzyme A dehydrogenase gene encodes a protein (i) or (ii) as follows: (i) having an amino acid sequence according to SEQ ID NO 2; (ii) derived by substituting, deleting or inserting one or more amino acids in the amino acid sequence defined by (i) and having the same function as that of the protein of (i). The present invention constructs genetically engineered *Mycobacterium* strains lacking of a hydroxyacyl-coenzyme A dehydrogenase gene or an acyl-coenzyme A thiolase gene, which are used in the preparation of steroidal compounds, such as 1,4-BNA, 4-BNA, 9-OH-BNA, etc. Further, the invention improves the production efficiency and product quality of steroidal drug, improves the utilization of drug precursors, reduces the production costs, and provides the advantages of mild reaction conditions, environmentally friendly, and high economic and social benefits.

1 Claim, 3 Drawing Sheets
Specification includes a Sequence Listing.

SEQUENCE LISTING

<160> NUMBER OF SEQ ID NOS: 16

<210> SEQ ID NO 1
<211> LENGTH: 2879

<212> TYPE: DNA
<213> ORGANISM: Mycobacterium neoaurum

<400> SEQUENCE: 1

```
atcggctgcg ccgagaccag tgcgacacgc tcgtggttga gctggttggt gaccagcttc    60
cagccggcgt tctcctcgcc gacgagggcg gatttgggaa cccggacgtc ctggtaatag   120
gttgcgctgg tatcgactcc ggacacggtg tgcaccggcg tccaggaaaa gccctcggca   180
gtggtgggca cgatcagcat cgagatgccg cggtgcttct tggcctcggg attggtgcgc   240
actgccagcc agacgtagtc ggcataggcg atcagcgagg tccacatctt ctgaccgttg   300
atcacataat cgtcaccatc gtgcaccgcg gtggtgcgca gcgaggcgag gtcggtgccg   360
gcgccgggtt cggaatagcc gatggagaag tgcaattggc ccgccgcgat tttcggcagg   420
aagaacttct tctgctcctc ggtgccgaaa tgcatgatcg tcggcgccac gctgttgatg   480
gtcaggaagg gcaccggcac attcgctatg gcggcttcgt cgttgaagat cagcccatcc   540
atcggcgggc gggcctggcc gccgtactcg gtcggccagg acagcgtcag ccagccgtcc   600
ttgcccatct gctcgacggt ttcgcggtat acgttcccgc ggcccatctc gccatcgctg   660
gccgccagcg cctcggcacg ttcgggagtc atcagtttgg tgaagtacga ccgcagttcg   720
cgacgcaact cctcctgctc ggcggtgtaa ccgatccgca tggcggcatc ctgtctgtct   780
gaggttgcgg ggcgaccggc cgaaaccggt tgcccgccga tatgctcgtt gtaacacgtt   840
ctagtcttgc ggtccagggc ggtaccgtta gcctgcacag gggcacacag cccgtgcccg   900
gagcgcgagg aggttcacat gcacgtagaa gtcgaccgtg accgctgcga aggtaatgcg   960
gtatgtgtcg ggatagcgcc cgacctgttc gatctcgatg acgaggacta tgccgtggtg  1020
aaagccgacc cggtacccgc cggccaggag gaactggccg aacaatccgt ggccgaatgc  1080
cctcgggcgg ccctgatccg tagagactag aggtattcat aaccgtgtcc cctgaagcag  1140
cgatgaacga caacccgatc gacctgtccg gaaaggttgc cgtcgtcacc ggcgcggccg  1200
ccggcctggg ccgggccgag gcgataggcc tggcgcgggc cggcgcgacg tcgtggtca   1260
acgacatggc cggcgcgctg gacaactccg acgtgctggc cgagatcgaa gcggtcgggt  1320
ccaagggcgt cgcggtcgcc ggtgatatca gcgcgcgcag caccgccgac gaactcgtcg  1380
agacagccga ccggctcggg ggactgggca tcgtggtgaa caacgccggc atcacccggg  1440
acaagatgct gttcaacatg tccgacgagg actgggacgc ggtgatcgcc gtgcatctgc  1500
gcggacactt cctgttgacg cgcaatgctg cggcgtactg gaaggcgaag gccaaggaga  1560
ccgccgacga acgggtgtac ggacggatcg tcaacacctc ctcggaggcc gggatcgccg  1620
gaccggtggg tcaagccaat tacggtgccg ccaaggccgg tatcacggcg ttgacgctgt  1680
cggcggcgcg cggttgagc aggtacgggg tgcgggccaa tgccatcgca ccgcgggccc  1740
gcaccgccat gaccgccggc gtgttcggtg atgcaccgga gctggcggac ggacaggtcg  1800
atgccctctc gccggagcat gtcgtcacgc tcgtcaccta cctgtcctcc ccggcgtccg  1860
aggatgtcaa cggcagctg ttcatcgtgt acggaccgac ggtcaccctg gttgcggcgc  1920
cggttgccgc ccaccggttc gatgccgccg gtgatgcctg gaccccgcg gcgttgagcg   1980
acacgctcgg tgacttcttt gctaaaaggg atccgaatat tgggttctcc gcaactgagc  2040
tcatgggttc ttgatttagg agaacggcat attcaccggt ccgggccgac tagaacctgt  2100
tctagaatga catccgtcac accggcgctg accaggaaaa atgcgagttt acaagaact   2160
tttcggttct ttgacactgt gaacgtgttc tagttactat gagcccgctc actatgaacg  2220
```

```
acgtgcacat cagggggtgga aagcccgccg gagcgaaccg tttcccgcta ttgtcgggtt    2280
cttcgccacg acgggacggc agccccactc gagaatggag tcgaggttga tcgaacagct    2340
ttcggctccg gcgcgagccg tgggtgggtt cgtcgagatg accatcgaca cgttcgtcaa    2400
gatgttccag cggccgtttc agttccgtga gttcctcgac cagacctgga tgatcgcgcg    2460
ggtctcgctg gttcccacgc tgctggtgtc gattccgttc accgtcctgg tcgctttcac    2520
cctcaacatc ctgctgcgcg agatcggtgc ggccgacctc tccggggccg gtaccgcgtt    2580
cggcaccatc acccagctgg gccggtggt gacggtgctc gtcgtcgcag gcgcgggcgc     2640
gaccgccatc tgtgccgacc tgggtgcccg aaccatccgc gaggagatcg acgcgatgcg    2700
ggtgctcggc atcgatccga tccagcgcct ggtggtgccg cgggtgctgg catcgacatt    2760
cgtcgcggtg ctgctcaacg ggttggtgtg cgcgatcggt ctgtcgggcg gctatgtgtt    2820
ctcggtgttc ctgcagggag tcaacccggg tgcgttcatc aacgggttga ccatcctga    2879
```

<210> SEQ ID NO 2
<211> LENGTH: 303
<212> TYPE: PRT
<213> ORGANISM: Mycobacterium neoaurum

<400> SEQUENCE: 2

```
Met Asn Asp Asn Pro Ile Asp Leu Ser Gly Lys Val Ala Val Val Thr
1               5                   10                  15

Gly Ala Ala Ala Gly Leu Gly Arg Ala Glu Ala Ile Gly Leu Ala Arg
            20                  25                  30

Ala Gly Ala Thr Val Val Val Asn Asp Met Ala Gly Ala Leu Asp Asn
        35                  40                  45

Ser Asp Val Leu Ala Glu Ile Glu Ala Val Gly Ser Lys Gly Val Ala
    50                  55                  60

Val Ala Gly Asp Ile Ser Ala Arg Ser Thr Ala Asp Glu Leu Val Glu
65                  70                  75                  80

Thr Ala Asp Arg Leu Gly Gly Leu Gly Ile Val Val Asn Asn Ala Gly
                85                  90                  95

Ile Thr Arg Asp Lys Met Leu Phe Asn Met Ser Asp Glu Asp Trp Asp
            100                 105                 110

Ala Val Ile Ala Val His Leu Arg Gly His Phe Leu Leu Thr Arg Asn
        115                 120                 125

Ala Ala Ala Tyr Trp Lys Ala Lys Ala Lys Glu Thr Ala Asp Gly Arg
    130                 135                 140

Val Tyr Gly Arg Ile Val Asn Thr Ser Ser Glu Ala Gly Ile Ala Gly
145                 150                 155                 160

Pro Val Gly Gln Ala Asn Tyr Gly Ala Ala Lys Ala Gly Ile Thr Ala
                165                 170                 175

Leu Thr Leu Ser Ala Ala Arg Gly Leu Ser Arg Tyr Gly Val Arg Ala
            180                 185                 190

Asn Ala Ile Ala Pro Arg Ala Arg Thr Ala Met Thr Ala Gly Val Phe
        195                 200                 205

Gly Asp Ala Pro Glu Leu Ala Asp Gly Gln Val Asp Ala Leu Ser Pro
    210                 215                 220

Glu His Val Val Thr Leu Val Thr Tyr Leu Ser Ser Pro Ala Ser Glu
225                 230                 235                 240

Asp Val Asn Gly Gln Leu Phe Ile Val Tyr Gly Pro Thr Val Thr Leu
                245                 250                 255

Val Ala Ala Pro Val Ala Ala His Arg Phe Asp Ala Ala Gly Asp Ala
```

|  | 260 | 265 | 270 |  |
|---|---|---|---|---|

Trp Asp Pro Ala Ala Leu Ser Asp Thr Leu Gly Asp Phe Phe Ala Lys
275 280 285

Arg Asp Pro Asn Ile Gly Phe Ser Ala Thr Glu Leu Met Gly Ser
290 295 300

<210> SEQ ID NO 3
<211> LENGTH: 3036
<212> TYPE: DNA
<213> ORGANISM: Mycobacterium neoaurum

<400> SEQUENCE: 3

```
gttccttctt gtagagctcc cactggtcgg gattgtcggc gaaggcgatc atgccgtggg     60
tgatcgagtt gcgggtggtc tcgttgcctg cgacggcaag catgaccacg aagaaaccga    120
actcgtcgtc agagagcttc tcgccctcga tatcggcctc gatcagcttg gtcacgatgt    180
cctcggtcgg gttctgcgcc cgctcctcgg ccatcttcat ggcgtaggtg atgagctcga    240
aggaggacat cgccggatcg acatcggcgt actcgggtgt ctcgcccgca gtcatctcat    300
tggaccagcg gaagatcttg tcccggtcgt cctgcggcac accgagcagt cggcgatgg     360
cctgcagcgg cagttcgcag acacctgctc gacgaagtc gcccgaaccg ctgccgccg      420
cggtttcggc gatcttgcgg gcacgggccc gcaactcgtc ttcgagccgt ccgatggcgc    480
gcggggtgaa cccgcgcgag atgatcttgc gcaaccgggt gtgctgcggc gcgtccatgt    540
tgagcaggac ggccttctgc agatcgatgg cgtcgcgggt catctcctgc ggccagaccg    600
ggatggcgcc gtcgggtgag ctgccgaaga tgtcgtttcg cttcgagacc tctttgacgt    660
cggcatgctt ggtgacgatc cagtagccct tgtcgccgaa gccccggtc ccttccggca    720
cgtccaccca gtgacggc tcggcgcgg gaatcctccg caactcctcc acgggcaggc      780
gttcgaggtt cagactggcg tccagcgggt cgaagcctt gggcaggttg ggctgggca     840
tgcagagatc tccttgctca aatcgggtca tgtcaccggc cacctcgggt gccgagacaa    900
ttccttctag taccactcgt gaaccattga acatgccttc accgcagat aaaaggcgcg    960
gcggcatcct cgcttgtcag agtaatgaaa cgtgttctag cctgacaagc atgggtaatc   1020
ctgtcatcgt cgaagccacc cgcagcccta tcggcaagcg caacggctgg ctgtccgggc   1080
tgcatgccac cgaactcttg ggcgccgtgc agaaggcggt cgtcgagaag gccgggatcg   1140
acgccggcga tgtcgaacag ctcatcggcg gttgtgtcac ccagtacggc gagcagtcca   1200
acaacatcac ccgggtcggc tggctgaccg cgggattgcc cgagcacgtg ggtgccacca   1260
ccatcgactg ccagtgcggc agcgcccagc aggccaacca tctgatcgcg ggccttatcg   1320
ccacgggtgc gatcgatatc ggcatcgcat gcggtatcga ggcgatgagc cgggtgggcc   1380
tgggcgccaa tgccggtccc gatcgcggtc tcatccgcgc ctcgtcttgg gatatcgaca   1440
tgcccaacca gttcgaggcc gccgagcgga tcgccaagcg ccgcgggatc acccgtgccg   1500
acctggacgc gttcgggctg gcctcgcagg ccaaggccaa gcaggcctgg gccgagggtc   1560
gcttcgatcg ggagatctca cccatctcag cgccggtgct cgacgagaac aagcgtccga   1620
ccgatgaatg ggcgctcgtg acccgcgatc aaggtctgcg cgataccacg gcggagggtc   1680
tggccgcgct gaagcccgtg atggaaggtg ccatgcacac cgcgggaacc tcctcgcaga   1740
tctccgacgg cgcggccgcg gtgctgtgga tggacagcga tgtggcgaag gcccacggcc   1800
tcacgccgcg cgcccggatc gtggcgcagg ccaatgtcgg tgccgagacc tactaccacc   1860
tcgacggccc ggtgcagtcg accgccaagg tgttggagaa ggccgggatg aagatgggcg   1920
```

```
atatcgacct cgtggagatc aacgaggctt tcgcgtccgt cgtgctgtcc tgggcgcagg    1980
tccacgaggc cgatatggac aaggtcaacg tcaacggtgg cgccatcgcg ctgggccacc    2040
cagtgggctc caccggtgcc cggttgatca ccaccgcact gcacgagctg agcgcaccg     2100 gtaagagcac cgcgctgatc acgatgtgcg ccggtggcgc gctgagcacg ggcaccatca    2160
tcgagcggat ctaagaccgc atggccgtct cggacgccga acggatcgcg cggcgcagt     2220 cctatatcga cgcgctgtcg acccatcgcg cggatgccgt cccatttcat ccggattgca    2280
tccgcatcga gatggggctc aagaccgggc ggtcgggaga tcacctgcgg cgcagcctga    2340
acaacggtcc gcagttcaag gtcatcgaaa agaccacgcc accggagttc accgtcgacg    2400
gggaccacat ccgtgctcgt ttcgacgtgc tgaccaagcc tcggctgttc ggcaggcgcg    2460
tgtgctccca gtcgacgag acgtttctga tccccgccca cgatcccggg atccaccaca     2520
tccgggcgtc gctcaagccg ttcatcagcc gttagggttt cggcatgccc acaccaccca    2580
agcctctgag ccccaaacag atcgaaggcc tcaactccaa gcggtcggc accggcatca     2640 aatggatgtc gcgtgccaat acctggctgt tcaagaagtc cggcggcaag ctcggcaaca    2700
aattcctgcg tggcgccgag gtaggcatcc tgaccaccac cggccgcaag tccggggagc    2760
cacgggacag tccgctgctg ttcctgcagg agggcaggcg catcgtgttg gtggcctccc    2820
aaggtggccg ggccaccaac ccgatgtggt acctgaacat caaggccgac ccgaacatca    2880
ccttccagac gaagaaggaa aagctcgacc tggtggcccg ggaggccacc gatgccgagc    2940
gcgacgagta ctggcccaag ctcgacgcca tgtaccccga cttcgcgaac taccggtcct    3000
acaccgatcg caagatcccg atcctgatct gcgacc                              3036
```

<210> SEQ ID NO 4
<211> LENGTH: 387
<212> TYPE: PRT
<213> ORGANISM: Mycobacterium neoaurum

<400> SEQUENCE: 4

```
Met Gly Asn Pro Val Ile Val Glu Ala Thr Arg Ser Pro Ile Gly Lys
1               5                   10                  15

Arg Asn Gly Trp Leu Ser Gly Leu His Ala Thr Glu Leu Leu Gly Ala
            20                  25                  30

Val Gln Lys Ala Val Val Glu Lys Ala Gly Ile Asp Ala Gly Asp Val
        35                  40                  45

Glu Gln Leu Ile Gly Gly Cys Val Thr Gln Tyr Gly Glu Gln Ser Asn
    50                  55                  60

Asn Ile Thr Arg Val Gly Trp Leu Thr Ala Gly Leu Pro Glu His Val
65                  70                  75                  80

Gly Ala Thr Thr Ile Asp Cys Gln Cys Gly Ser Ala Gln Gln Ala Asn
                85                  90                  95

His Leu Ile Ala Gly Leu Ile Ala Thr Gly Ala Ile Asp Ile Gly Ile
            100                 105                 110

Ala Cys Gly Ile Glu Ala Met Ser Arg Val Gly Leu Gly Ala Asn Ala
        115                 120                 125

Gly Pro Asp Arg Gly Leu Ile Arg Ala Ser Ser Trp Asp Ile Asp Met
    130                 135                 140

Pro Asn Gln Phe Glu Ala Ala Glu Arg Ile Ala Val Arg Arg Gly Ile
145                 150                 155                 160

Thr Arg Ala Asp Leu Asp Ala Phe Gly Leu Ala Ser Gln Ala Lys Ala
                165                 170                 175
```

Lys Gln Ala Trp Ala Glu Gly Arg Phe Asp Arg Glu Ile Ser Pro Ile
            180                 185                 190

Ser Ala Pro Val Leu Asp Glu Asn Lys Arg Pro Thr Asp Glu Trp Ala
        195                 200                 205

Leu Val Thr Arg Asp Gln Gly Leu Arg Asp Thr Ala Glu Gly Leu
    210                 215                 220

Ala Ala Leu Lys Pro Val Met Glu Gly Ala Met His Thr Ala Gly Thr
225                 230                 235                 240

Ser Ser Gln Ile Ser Asp Gly Ala Ala Val Leu Trp Met Asp Ser
            245                 250                 255

Asp Val Ala Lys Ala His Gly Leu Thr Pro Arg Ala Arg Ile Val Ala
            260                 265                 270

Gln Ala Asn Val Gly Ala Glu Thr Tyr Tyr His Leu Asp Gly Pro Val
        275                 280                 285

Gln Ser Thr Ala Lys Val Leu Glu Lys Ala Gly Met Lys Met Gly Asp
    290                 295                 300

Ile Asp Leu Val Glu Ile Asn Glu Ala Phe Ala Ser Val Val Leu Ser
305                 310                 315                 320

Trp Ala Gln Val His Glu Ala Asp Met Asp Lys Val Asn Val Asn Gly
            325                 330                 335

Gly Ala Ile Ala Leu Gly His Pro Val Gly Ser Thr Gly Ala Arg Leu
        340                 345                 350

Ile Thr Thr Ala Leu His Glu Leu Glu Arg Thr Gly Lys Ser Thr Ala
    355                 360                 365

Leu Ile Thr Met Cys Ala Gly Gly Ala Leu Ser Thr Gly Thr Ile Ile
370                 375                 380

Glu Arg Ile
385

<210> SEQ ID NO 5
<211> LENGTH: 36
<212> TYPE: DNA
<213> ORGANISM: Artificial Sequence
<220> FEATURE:
<223> OTHER INFORMATION: primer for knockout of hydroxyacyl-coenzyme a
      dehydrogenase gene

<400> SEQUENCE: 5
tatactgcag tatcggctgc gccgagacca gtgcga                                36

<210> SEQ ID NO 6
<211> LENGTH: 35
<212> TYPE: DNA
<213> ORGANISM: Artificial Sequence
<220> FEATURE:
<223> OTHER INFORMATION: primer for knockout of hydroxyacyl-coenzyme A
      dehydrogenase gene

<400> SEQUENCE: 6
tcgcgaattc cacgacggca acctttccgg acagg                                 35

<210> SEQ ID NO 7
<211> LENGTH: 35
<212> TYPE: DNA
<213> ORGANISM: Artificial Sequence
<220> FEATURE:
<223> OTHER INFORMATION: primer for knockout of hydroxyacyl-coenzyme A
      dehydrogrenase gene

<400> SEQUENCE: 7

```
gcgcgaattc aacgggcagc tgttcatcgt gtacg                                35
```

<210> SEQ ID NO 8
<211> LENGTH: 35
<212> TYPE: DNA
<213> ORGANISM: Artificial Sequence
<220> FEATURE:
<223> OTHER INFORMATION: primer for knockout of hydroxyacyl-coenzye A
      dehydrogenase gene

<400> SEQUENCE: 8

```
cgcgaagctt tcaggatggt caacccgttg atgaa                                35
```

<210> SEQ ID NO 9
<211> LENGTH: 35
<212> TYPE: DNA
<213> ORGANISM: Artificial Sequence
<220> FEATURE:
<223> OTHER INFORMATION: primer for knockout of acyl-coenzyme A thiolase
      gene

<400> SEQUENCE: 9

```
gcgcaagctt gttccttctt gtagagctcc cactg                                35
```

<210> SEQ ID NO 10
<211> LENGTH: 35
<212> TYPE: DNA
<213> ORGANISM: Artificial Sequence
<220> FEATURE:
<223> OTHER INFORMATION: primer for knockout of acyl-coenzyme A thiolase
      gene

<400> SEQUENCE: 10

```
tatagaattc gtactgggtg acgcagccgc cgatg                                35
```

<210> SEQ ID NO 11
<211> LENGTH: 35
<212> TYPE: DNA
<213> ORGANISM: Artificial Sequence
<220> FEATURE:
<223> OTHER INFORMATION: primer for knockout of acyl-coenzyme A thiolase
      gene

<400> SEQUENCE: 11

```
gcgcgaattc gacatggaca aggtcaacgt caacg                                35
```

<210> SEQ ID NO 12
<211> LENGTH: 37
<212> TYPE: DNA
<213> ORGANISM: Artificial Sequence
<220> FEATURE:
<223> OTHER INFORMATION: primer for knockout of acyl-coenzyme A thiolase
      gene

<400> SEQUENCE: 12

```
tatagcggcc gcggtcgcag atcaggatcg ggatctt                              37
```

<210> SEQ ID NO 13
<211> LENGTH: 25
<212> TYPE: DNA
<213> ORGANISM: Artificial Sequence
<220> FEATURE:
<223> OTHER INFORMATION: hydroxyacyl-coenzyme A dehydrogenase gene
      knockout validation primer

<400> SEQUENCE: 13

```
<210> SEQ ID NO 14
<211> LENGTH: 25
<212> TYPE: DNA
<213> ORGANISM: Artificial Sequence
<220> FEATURE:
<223> OTHER INFORMATION: hydroxyacyl-coenzyme A dehydrogenase gene
      knockout validation primer

<400> SEQUENCE: 14
tagtcggccc ggaccggtga atatg                                            25

<210> SEQ ID NO 15
<211> LENGTH: 26
<212> TYPE: DNA
<213> ORGANISM: Artificial Sequence
<220> FEATURE:
<223> OTHER INFORMATION: acyl-coenzyme A thiolase gene knockout
      validation primer

<400> SEQUENCE: 15
tcagagtaat gaaacgtgtt ctagcc                                           26

<210> SEQ ID NO 16
<211> LENGTH: 24
<212> TYPE: DNA
<213> ORGANISM: Artificial Sequence
<220> FEATURE:
<223> OTHER INFORMATION: acyl-coenzyme A thiolase gene knockout
      validation primer

<400> SEQUENCE: 16
atccggatgc agtccggatg gaat                                             24
```

HYDROXYACYL-COENZYME A DEHYDROGENASE GENE, AN ACYL-COENZYME A THIOLASE GENE, GENETICALLY ENGINEERED STRAINS AND A USE THEREOF

BACKGROUND

The Sequence Listing associated with this application is hereby incorporated by reference as found in ASCII text file named SequenceListing_ST25.txt created on Nov. 25, 2017 and having a size in bytes of 17,069.

TECHNICAL FIELD

The present invention relates to technical field of genetic engineering, more particularly, to a hydroxyacyl-coenzyme A dehydrogenase gene, an acyl-coenzyme A thiolase gene, genetically engineered strains and a use thereof.

RELATED ART

Steroidal compound, also known as steroid, is a class of compounds having perhydrocyclopentanophenanthrene as mother nucleus and having similar structures. As illustrated below, the basic structure is consisting of three six-membered rings and a five-membered ring, respectively known as A, B, C, and D ring, has methyl groups at positions 10 and 13 of the mother nucleus, may has hydroxyl, keto or alkyl groups at positions 3, 11, and 17, may has double bond on A, B, C, and D rings, and usually has a side chain with different length at position 17. Due to the differences of substituent groups, position of double bond or three-dimensional configuration, etc. on steroidal nucleus, a series of compounds with unique physiological functions are produced. In humans and animals, steroids are the main endogenous hormones, which are secreted by sexual organs and adrenal cortex, and are closely related to reproduction, brain and bone development, steady state maintenance and regulation of biological effects and so on. As exogenous hormones, steroid hormone drugs also are a class of indispensable clinical drugs, which play an important regulation role to the body, and have extremely important medical value, for example, adrenal cortex hormones have anti-inflammatory, antiallergic, antiallergy, anti-shock response and other effects.

Figure 1:
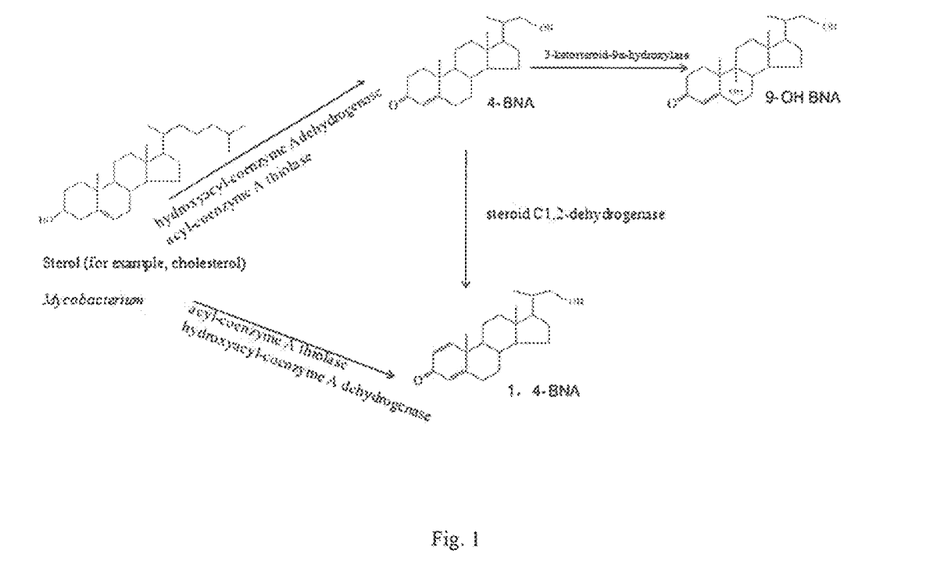
FIG. 1 shows schematic diagram of equation and key enzymes of microbial degradation of sterols for preparing 4-BNA, 1,4-BNA, 9-OH-BNA.

As shown in FIG. 1, the hydroxyacyl-coenzyme A dehydrogenase and acyl-coenzyme A thiolase are two key enzymes involved in the degradation of sterol side chains by *Mycobacteria*. The function of hydroxyacyl-coenzyme A dehydrogenase in the steroid metabolic gene cluster of *Mycobacterium tuberculosis* is defined as a 17β-hydroxyl-steroid dehydrogenase, so named because it is highly approximate to N segment functional domain of mammalian cell type IV 17β-hydroxysteroid dehydrogenase. Meanwhile, it has also been reported but so far has not been confirmed that the enzyme has 3-hydroxyacyl-coenzyme A dehydrogenase function. The acyl-coenzyme A thiolase is involved in the thiolysis decarburization reaction of sterol side chain degradation, which is similar to thioclastic reaction in the β-oxidation process of fatty acids. The sterol side chain degradation is an extremely complex enzymatic process, the mechanism of which remains to be further explored.

Microbial transformations are key steps in the production process of steroids in the pharmaceutical industry. The outdated production process, the limited efficient of strains, the heavy investment on the construction of new production line and other issues thereof seriously restricts the rapid development of microbial transformations in the steroidal pharmaceutical industry, which also are important reasons for the high cost of steroidal drug production. There are many steroidal pharmaceutical production enterprises in China, and their output is huge. Thus, the development of high efficient strains for some of the current important steroid microbial transformation reactions will be welcomed by the industry, which will in general greatly enhance steroid medicine industry production level, and the resulting economic benefits will be very impressive.

As to the important microbial transformation reactions in the steroidal pharmaceutical industry, the development of improved microbial transformation reactions through genetic engineering modification will greatly improve the production efficiency and product quality of steroidal drugs, help to reduce the energy consumption of steroidal drug production process, improve the utilization of drug precursors, simplify the production steps and reduce the production costs, thereby contribute to the decline in steroidal drug prices. In addition, the microbial transformation conditions are mild and environmentally friendly, belonging to a green chemical technology, and thus, it is the inevitable requirement of social sustainable development to vigorously promote its application in the industry.

SUMMARY OF THE INVENTION

It is an object of the present invention to provide a hydroxyacyl-coenzyme A dehydrogenase gene, an acyl-coenzyme A thiolase gene, genetically engineered strains and a use thereof, so as to solve the problems that the production process of the steroidal pharmaceutical industry in the prior art is complicated, low efficiency, high cost, and then leads to steroidal drug prices expensive.

In order to solve the above technical problems, the present invention adopts the following technical solution:

A first aspect of the present invention provides a hydroxyacyl-coenzyme A dehydrogenase gene, said hydroxyacyl-coenzyme A dehydrogenase gene encodes a protein (i) or (ii) as follows: (i) having an amino acid sequence according to SEQ ID NO 2; (ii) derived by substituting, deleting or inserting one or more amino acids in the amino acid sequence defined by (i) and having the same function as that of the protein of (i).

Preferably, the protein encoded by the hydroxyl-coenzyme A dehydrogenase gene has at least 75% of homology to the amino acid sequence shown in SEQ ID NO: 2. More preferably, 80% or more, and more preferably 90% or more.

The hydroxyacyl-coenzyme A dehydrogenase gene has the following sequence (1) or (2): (1) having a nucleotide sequence shown at positions 1143-2054 of the sequence according to SEQ ID NO 1; (2) having a nucleotide sequence that is at least 70% homology to the nucleotide sequence shown in the sequence (1). More preferably, the hydroxyacyl-coenzyme A dehydrogenase gene has a nucleotide sequence that is at least 87% homology to the sequence shown at positions 1143-2054 of the sequence according to SEQ ID NO 1, or has a nucleotide sequence that is at least 60% identity to the sequence according to SEQ ID NO 1. The remaining nucleotide sequence of the sequence according to SEQ ID NO 1 contains the regulatory element and the adjacent gene fragment of the enzyme.

The hydroxyacyl-coenzyme A dehydrogenase gene is derived from *Actinomycetes*, preferably, strains of *Mycobacterium* and strains of *Rhodococcus*.

Preferably, the hydroxyacyl-coenzyme A dehydrogenase gene is derived from strains of *Mycobacterium*.

More preferably, the strains of *Mycobacterium* are fast growing type of *Mycobacterium*.

Furthermore, the fast growing type of *Mycobacterium* is selected from the group consisting of *Mycobacterium* sp. NRRL B-3683, *Mycobacterium* sp. NRRLB-3805, *Mycobacterium smegmatism*, *Mycobacterium fortuitum*, *Mycobacterium gilvum*, *Mycobacterium neoaurum*, *Mycobacterium Phlei*, *Mycobacterium aviumn* or *Mycobacterium vanbaalenii*.

Furthermore, the fast growing type of *Mycobacterium* microorganism is *Mycobacterium neoaurum*.

Most preferably, the hydroxyacyl-coenzyme A dehydrogenase gene is derived from the fast growing type of *Mycobacterium neoaurum* NwIB-00.

A second aspect of the present invention provides an acyl-coenzyme A thiolase gene, said acyl-coenzyme A thiolase gene encodes a protein (iii) or (iv) as follows: (iii) having an amino acid sequence according to SEQ ID NO 4; (iv) derived by substituting, deleting or inserting one or more amino acids in the amino acid sequence defined by (iii) and having the same function as that of the protein of (iii).

The acyl-coenzyme A thiolase gene encodes a protein having at least 70% homology to the amino acid sequence according to SEQ ID NO 4, more preferably, 80% or more.

The acyl-coenzyme A thiolase gene has the following sequence (3) or (4): (3) having a nucleotide sequence shown at positions 1010-2174 of the sequence according to SEQ ID NO 3; (4) having a nucleotide sequence that is at least 70% homology to the nucleotide sequence shown in the sequence (3), more preferably, 87% identity or more.

The acyl-coenzyme A thiolase gene has a nucleotide sequence that is at least 60% homology to the sequence according to SEQ ID NO 3.

The acyl-coenzyme A thiolase gene is derived from *Actinomycetes*.

Preferably, the *Actinomycetes* comprise strains of *Mycobacterium* and strains of *Rhodococcus*.

More preferably, the *Mycobacterium* microorganism is a fast growing type of *Mycobacterium*.

Furthermore, the fast growing type of *Mycobacterium* is selected from the group consisting of *Mycobacterium* sp. NRRL B-3683, *Mycobacterium* sp. NRRLB-3805, *Mycobacterium smegmatism*, *Mycobacterium fortuitum*, *Mycobacterium gilvum*, *Mycobacterium neoaurum*, *Mycobacterium Phlei*, *Mycobacterium avium* or *Mycobacterium vanbaalenii*.

Most preferably, the acyl-coenzyme A thiolase gene is derived from the fast growing type of *Mycobacterium neoaurum* NwIB-00.

A third aspect of the present invention provides a kind of genetically engineered *Mycobacterium* strains, which are *Mycobacteria* that lack of the hydroxyacyl-coenzyme A dehydrogenase gene or acyl-coenzyme A thiolase gene. It is characterized that, they are obtained by mutation and homologous recombination of the above mentioned hydroxyacyl-coenzyme A dehydrogenase gene or acyl-coenzyme A thiolase gene. That is, through the inactivation of the hydroxyl-coenzyme A dehydrogenase gene and/or the inactivation of the acyl-coenzyme A thiolase function by gene manipulation, constructing genetically engineered *Mycobacterium* strains without the activity of the hydroxyl-coenzyme A dehydrogenase gene or without the activity of the acyl-coenzyme A thiolase, which are achieved by a targeted, unlabeled genetic engineering operation of the hydroxyl-coenzyme A dehydrogenase gene and/or the acyl-coenzyme A thiolase gene.

Preferably, the invention also provides genetically engineered *Mycobacterium* strains, which are *Mycobacteria* that simultaneously lack of 3-ketosteroid-9α-hydroxylase gene and the hydroxyacyl-coenzyme A dehydrogenase gene.

It is also preferred that the genetically engineered *Mycobacterium* strains are *Mycobacteria* that simultaneously lack of 3-ketosteroid-$\Delta^1$-dehydrogenase gene and the hydroxyacyl-coenzyme A dehydrogenase gene.

It is further preferred that the genetically engineered *Mycobacterium* strains are *Mycobacteria* that simultaneously lack of 3-ketosteroid-9α-hydroxylase gene and the hydroxyacyl-coenzyme A dehydrogenase gene and 3-ketosteroid-$\Delta^1$-dehydrogenase gene.

It is also preferred that the genetically engineered *Mycobacterium* strains are *Mycobacteria* that simultaneously lack of 3-ketosteroid-9α-hydroxylase gene and the acyl-coenzyme A thiolase gene.

A fourth aspect of the invention provides a use of above genetically engineered *Mycobacterium* strains in the preparation of steroidal compounds.

The steroidal compounds comprise: 22-hydroxy-23,24-bisnorchol-1,4-dien-3-one, 22-hydroxy-23,24-bisnorchol-4-ene-3-one and 9α,22-dihydroxy-23,24-bisnorchol-4-ene-3-one.

In view of the above, the present invention provides a hydroxyacyl-coenzyme A dehydrogenase gene and an acyl-coenzyme A thiolase gene, and a variety of engineered strains obtained by constructing various carriers and transforming the relevant strains, for example, a *Mycobacterium* without hydroxyacyl-coenzyme A dehydrogenase activity and without acyl-coenzyme A thiolase activity. It can be selectively to prepare 22-hydroxy-23,24-bisnorchol-1,4-dien-3-one (1,4-BNA), 22-hydroxy-23,24-bisnorchol-4-ene-3-one (4-BNA) and 9α,22-dihydroxy-23,24-bisnorchol-4-ene-3-one (9-OH-BNA) using these engineered strains, which greatly improves the production efficiency of steroidal drugs, helps to reduce the energy consumption of steroidal drug production process, improves the utilization of drug precursors, simplifies the production steps and reduces production costs, and the reaction conditions are mild and environmentally friendly, worthy of being widely popularized, having high economic and social benefits. This kind of potential and valuable new precursor compounds can be used to produce adrenal corticosteroids, especially progesterone, through simple chemical reactions. If it is popularized, it will greatly improve the backward status of existing adrenal cortex products production process.

DETAILED DESCRIPTION OF THE PREFERRED EMBODIMENTS

In order to better understand the present invention, the invention is further described in connection with following specific embodiments. It should be understood that the following examples are intended to illustrate the invention and are not intended to limit the scope of the invention.

The experimental methods, if no specific condition is indicated, in the following examples, are generally carried out according to conventional conditions, as described in Molecular Cloning: Laboratory Manual (New York: Cold Spring Harbor Laboratory Press, 1989).

The gene manipulation technique employed in the present invention is mainly an unlabeled enzyme function inactivation technique. The unlabeled enzyme function inactivation technology mainly comprises: non-resistant markers in-frame deletion of hydroxyacyl-coenzyme A dehydrogenase gene or acyl-coenzyme A thiolase gene.

The *Escherichia coli* DH5a and pMD19-T vectors used in the examples of the present invention were purchased from Novagen Corporation and the primers were synthesized by Takara Corporation.

The steroidal substrate used in the present invention is 3-alcohol-5-ene-steroids, only for example, "sterols" as a class of 3-alcohol-5-ene-steroids. The sterols are usually derived from plants and animals, such as cholesterol and phytosterols, wherein the cholesterol can be derived from animal fats, and the phytosterols are available in a variety of sources, such as deodorant distillate from vegetable oil processing, and tall oil from the pulp and paper industry. The phytosterols are generally a mixture, usually contain sitosterol, stigmasterol, campesterol and brassicasterol. Some of the sterols may also be derived from microorganisms, such as, ergosterol and the like.

The *Mycobacteria* referred to in the present invention are non-pathogenic fast growing *Mycobacteria*. In order to better understand the present invention, a standard strain NwIB-00 (Accession No. as follows: ATCC 25795) of *Mycobacterium neoaurum* is used as a specific embodiment for further illustration. It should be understood that the following examples are intended to illustrate the invention and are not intended to limit the scope of the invention.

Example 1 Construction of Engineered Strains by Deleting Bydroxyacyl-Coenzyme A Dehydrogenase Gene or Acyl-Coenzyme A Thiolase Gene Based on *Mycobacterium* NwIB-00

In the present example, the main technical means and method of homologous recombination and double exchange knockout used in *Mycobacteria* are described by taking the knockout of the hydroxyacyl-coenzyme A dehydrogenase gene as an example, and the knockout of the acyl-coenzyme A thiolase gene is completed by the same method. There are a variety of methods for *Mycobacterium* gene knockout, and the method of gene knockout is not limited here. A gene knockout method developed by Professor Tanya Parish is used as an example here to illustrate the target gene knockout (Bhavna G Gordhan And Tanya Parish. Gene replacement using pretreated DNA. *Mycobacterium tuberculosis* protocols. 2001, pp 77-92).

*Mycobacterium* hydroxy-coenzyme A dehydrogenase gene knockout plasmid is constructed, and then is electrotransformed into *Mycobacterium*. Screening is carried out with kanamycin and hygromycin, and then re-screened with sucrose plate to obtain gene knockout recombinants. The recombinants are validated by PCR. The present invention is directed to one or more genes knockout of the hydroxyacyl-coenzyme A dehydrogenase gene, the 3-ketosteroid-9α-hydroxylase gene, the 3-ketosteroid-$\Delta^1$-dehydrogenase gene, and the acyl-coenzyme A thiolase gene from *Mycobacterium* NwIB-00, to obtain six different *Mycobacterium* strains, named in turn, NwIB-X01, NwIB-X02, NwIB-X03, NwIB-X04, NwIB-X05, NwIB-X06.

Among them, the NwIB-X01 strain is obtained by the knockout of the 3-ketosteroid-9α-hydroxylase gene (kshA1) and the hydroxyacyl-coenzyme A dehydrogenase gene (hsd4A) (there is no order for knockout) from the NwIB-00 strain, which cannot degrade the steroidal mother nucleus, that is to say, one 3-ketosteroid-9α-hydroxylase gene and one hydroxyacyl-coenzyme A dehydrogenase gene, i.e., kshA1+hsd4A are knocked out.

NwIB-X02 strain is obtained by the knock out of the 3-ketosteroid-$\Delta^1$-dehydrogenase gene from the NwIB-X01 strain, that is to say, one 3-ketosteroid-9α-hydroxylase gene, one hydroxyacyl-coenzyme A hydrogenase gene, and one 3-ketosteroid-$\Delta^1$-dehydrogenase gene (kstd1), i.e., kshA1+hsd4A+kstd1 are knocked out.

NwIB-X03 strain is a derivative of NwIB-X02 and is obtained on the basis of the NwIB-X02 strain by the knockout of other two 3-ketosteroid-$\Delta^1$-dehydrogenase genes, that is to say, one 3-ketosteroid-9α-hydroxylase gene, one hydroxyacyl-coenzyme A dehydrogenase gene, and three 3-ketosteroid-$\Delta^1$-dehydrogenase genes, i.e., kshA1+hsd4A+kstd1+kstd2+kstd3 are knocked out.

NwIB-X04 strain is obtained by the knockout of the 3-ketosteroid-$\Delta^1$-dehydrogenase gene and the hydroxyacyl-coenzyme A dehydrogenase gene from the NwIB-00 strain (there is no order for knockout), that is to say, one hydroxyacyl-coenzyme A dehydrogenase gene, and one 3-ketosteroid-$\Delta^1$-dehydrogenase gene, i.e., hsd4A+kstd1 are knocked out.

NwIB-X05 strain is a derivative of NwIB-X04 and is obtained by the knockout of other two 3-ketosteroid-$\Delta^1$-dehydrogenase genes from the NwIB-X04 strain, that is to say, one hydroxy-coenzyme A dehydrogenase gene, and three 3-ketosteroid-1-dehydrogenase genes, i.e., hsd4A+kstd1+kstd2+kstd3 are knocked out.

NwIB-X06 strain is obtained by the knockout of the 3-ketosteroid-9α-hydroxylase gene and the acyl-coenzyme A thiolase gene from the NwIB-00 strain, that is to say, one 3-ketosteroid-9α-hydroxylase gene and one acyl-coenzyme A thiolase gene, i.e., kshA1+fadA5 are knocked out.

Wherein, the sequence and knockout method for the 3-ketosteroid-9α-hydroxylase gene (kshA1) can be specifically found in the patent specification of Application CN200910051613.7, which will not be described here.

Among them, these three kinds of 3-ketosteroid-Δ$^1$-dehydrogenase (kstd1, kstd2, kstd3) are isozyme having similar sequence, and the sequence and knockout method can be found in the patent specification of Application CN200910051615.6, which will not be described here.

1.1 The Acquisition of Upstream and Downstream Sequences Adjacent to Hydroxyacyl-Coenzyme A Dehydrogenase Gene and the Construction of Knockout Plasmid The whole genome of *Mycobacterium* NwIB-00 was sequenced and annotated. Then the complete reading frame sequence of hydroxyacyl-coenzyme A dehydrogenase gene was founded in combination with the reported gene cluster information of similar strains. The upstream and downstream sequences adjacent to hydroxyacyl-coenzyme A dehydrogenase gene were obtained. Based on the upstream and downstream sequences, the upstream and downstream primers for the knockout of the hydroxyacyl-coenzyme A dehydrogenase gene were designed using the software Oligo 6.0 and Primer 5.0 as follows:

```
                                          SEQ ID NO. 5
Q-hsd4A-uF: TATACTGCAGTATCGGCTGCGCCGAGACCAGTGCGA SEQ ID NO. 6
Q-hsd4A-uR: TCGCGAATTCCACGACGGCAACCTTTCCGGACAGG SEQ ID NO. 7
Q-hsd4A-dF: GCGCGAATTCAACGGGCAGCTGTTCATCGTGTACG SEQ ID NO. 8
Q-hsd4A-dR: CGCGAAGCTTTCAGGATGGTCAACCCGTTGATGAA
```

The upstream and downstream fragments of the hydroxyacyl-coenzyme A dehydrogenase gene were obtained by PCR amplification using the *M. neoaurum* NwIB-00 genome as template. The upstream and downstream genes of the target gene were respectively cloned into pMD19-T vector, and then digested with PstI, EcoRI, EcoRI, HindIII respectively, and the digested products were ligated to the corresponding digested *Mycobacterium* gene knockout plasmid pNL. The above mentioned plasmid and pGOAL19 plasmid were digested with PacI and connected non-directionally to construct the gene knockout plasmid QC-hsd4A.

1.2 The Acquisition of Upstream and Downstream Sequences Adjacent to Acyl-Coenzyme A Thiolase Gene and the Construction of Knockout Plasmid According to the method of Example 1.1, the upstream and downstream primers for knockout of the acyl-coenzyme A thiolase gene (fadA5) were designed as follows:

```
                                          SEQ ID NO. 9
Q-fadA5-uF: GCGCaagcttGTTCCTTCTTGTAGAGCTCCCACTG SEQ ID NO. 10
Q-fadA5-uR: TATAgaattcGTACTGGGTGACGCAGCCGCCGATG SEQ ID NO. 11
Q-fadA5-dF: GCGCgaattcGACATGGACAAGGTCAACGTCAACG SEQ ID NO. 12
Q-fadA5-dR: TATAgcggccgcGGTCGCAGATCAGGATCGGGATCTT
```

The upstream and downstream fragments of the acyl-coenzyme A thiolase gene were obtained by PCR amplification using the NwIB-00 genome as template. The upstream and downstream genes of the target gene were respectively cloned into pMD19-T vector, and then digested with HindIII, EcoRI, EcoRI, NotI respectively, and the digested products were ligated to the corresponding digested *Mycobacterium* gene knockout plasmid p2NIL. The above mentioned plasmid and pGOAL19 plasmid were digested with PacI and connected non-directionally to construct the gene knockout plasmid QC-fadA5.

1.3 Transformation of the Knockout Plasmid into *Mycobacterium* Competent Cells

*Mycobacterium* competent preparation: a first grade seed was incubated to OD 0.5-1.5, 5%-10% was transferred into second grade seed; after 14-24 h, adding 2% glycine to continue culture for about 24 h. The cells were collected by centrifugation and washed with 10% glycerol four times to suspend and then centrifuged. Finally, 1 ml of glycerol were added to the suspend cells and stored separately.

Electro-transformation: 10 μl of the above mentioned plasmid treated by alkali was added to 100 μl of the competent cells for 15 min and the shock conditions were as follows: 2.5 kv/cm, 25 μF, 20 ms.

1.4 Screening and Validation of Recombinants

The electro-transformation product was added to medium for renewing culture about 3-24 h, and then coated on solid medium (ingredient: hyg 50 μg/ml, Kn 20 μg/ml, X-gal 50 μg/ml) at 30° C. for 3-7 days. Colonies with blue spot were picked out for PCR validation. The verified single cross over (SCO) recombinants were coated on 2% sucrose plate and cultured at 30° C. for 3-7 days. The white colonies were picked out and verified by PCR.

Confirmation of recombinants: including PCR validation of single cross over recombinants and double cross over recombinants, and the principle of validation is described in the above cited literature. The hydroxyacyl-coenzyme A dehydrogenase gene knockout validation primers are shown as below:

```
                                          SEQ ID NO. 13
Q-hsd4A-YZ-F: ACGTAGAAGTCGACCGTGACCGCTG SEQ ID NO. 14
Q-hsd4A-YZ-R: TAGTCGGCCCGGACCGGTGAATATG
```

Figure 2:
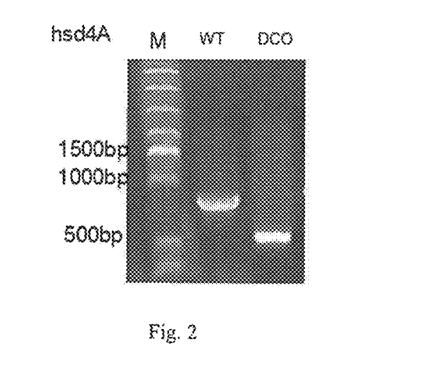
FIG. 2 shows a hydroxyacyl-coenzyme A dehydrogenase (hsd4A)-deficient strain is obtained through two-step screening of *Mycobacterium* transformants by the application of existing screening techniques, wherein M is the DNA standard marker; DCO is the amplification result of screened strain with deleted hsd4A gene by double exchange; and wt is the PCR amplification result of origin strain with the same primers.

The results of the validation are as shown in FIG. 2. As to the strain that has not been successfully knocked out the hydroxyacyl-coenzyme A dehydrogenase gene, only a band of about 1200 bp appears theoretically; and as to the strain that has been successfully knocked out the hydroxyacyl-coenzyme A dehydrogenase gene by double cross over (DCO) recombination, only a band of about 500 bp appears theoretically. As to the strain that has been successfully knocked out the hydroxyacyl-CoA dehydrogenase gene by single cross over (SCO) recombination, there are two bands of about 500 bp and 1200 bp theoretically, indicating that the hydroxyacyl coenzyme A dehydrogenase gene has been successfully knocked out and the function of the original enzyme has been destroyed.

The acyl-coenzyme A thiolase gene knockout validation primers are shown as below:

SEQ ID NO. 15
Q-fadA5-YZ-F: TCAGAGTAATGAAACGTGTTCTAGCC

SEQ ID NO. 16
Q-fadA5-YZ-R: ATCCGGATGCAGTCCGGATGGAAT

Figure 3:
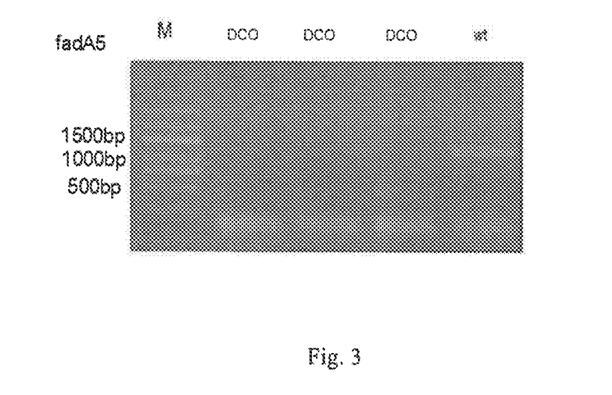
FIG. 3 shows an acyl-coenzyme A thiolase (fadA5)-deficient strain is obtained through two-step screening of *Mycobacterium* transformants by the application of existing screening techniques, wherein M is the DNA standard marker; DCO is the amplification result of screened strain with deleted hsd4A gene by double exchange; and wt is the PCR amplification result of origin strain with the same primers.

The results of the validation are as shown in FIG. 3. As to the strain that has not been successfully knocked out the acyl-coenzyme A thiolase gene, only a band of about 1300 bp appears theoretically; and as to the strain that has been successfully knocked out the acyl-coenzyme A thiolase gene by double cross over (DCO) recombination, only a band of about 500 bp appears theoretically, indicating that the acyl-coenzyme A thiolase gene has been successfully knocked out, and the function of the original enzyme has been destroyed.

Example 2 the Transformation of Steroids by Mycobacterium NwIB-00 and the Analysis Method of Results The sterol substrate was solubilized with 1% to 10% surfactant, polymer or organic solvent (such as Tween 80, ethanol, silicone oil, soybean oil, etc.). Using secondary or tertiary culture as seed, 5% to 10% of the seed was inoculated to the final transformation medium, and the sterol substrate can be added at any time. The conditions for steroid transformation were as follows: incubation temperature of 25-37° C., high dissolved oxygen value, and pH between 5.0 and 8.0. The end time of the conversion reaction was determined by thin layer chromatography (TLC) or gas chromatography (GC) analysis. After the reaction, the steroid conversion products can be extracted with the same volume of ethyl acetate, or chloroform and other organic solvents three times. The obtained solution was combined and vacuum dried. Then, the analysis and product preparation were conducted.

Shake-flask cultivation was adopted to cultivate Mycobacterium NwIB-00 to converse phytosterols, using 5%-10% of Tween80 or silicone oil as a cosolvent of phytosterol, in a 250 ml shake flask with 30 ml volume of sample loading, wherein 5%-10% of the seed was inoculated to a second grade culture containing 0.4-2 g/l of phytosterol. The culture conditions were as follows: 26-35° C., 200-300 rpm, pH5.0-8.0, for 3-7 days. The extraction of ethyl acetate was carried out, and the organic phase was detected by TLC and GC to check the transformation of steroids.

The operating conditions of the thin layer chromatography (TLC) were as follows: petroleum ether:ethyl acetate (6:4 to 7:3) was used as the developing agent; the thin plate was 5×10 cm prefabricated plate produced by Yantai Silicone Factory; 20% sulfuric acid solution was evenly sprayed; and the plate was baked 5 min-10 min in the 105° C. oven until the spots show up for observation.

Figure 4:
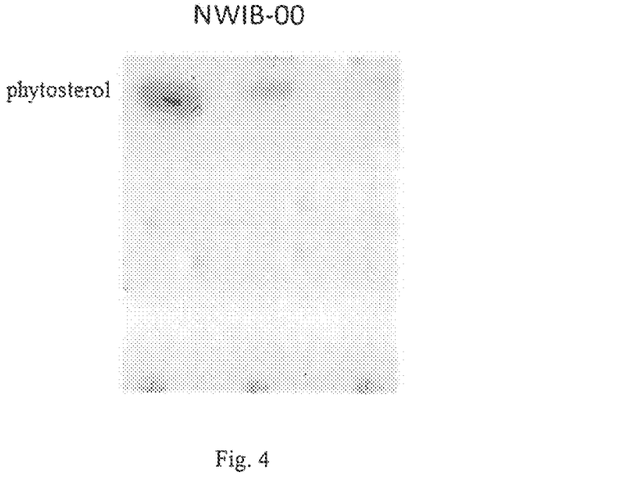
FIG. 4 is a thin layer chromatogram (TLC) of the transformation results of phytosterols by *Mycobacterium* NwIB-00.

The results of the transformation of phytosterols by Mycobacterium NwIB-00 are as shown in FIG. 4. Phytosterols can be completely decomposed and metabolized by Mycobacterium NwIB-00, without the accumulation of 1,4-BNA, 4-BNA, 9-OH-BNA and other products.

Example 3 the Preparation of 1,4-BNA, 4-BNA, 9-OH-BNA from the Degradation of Sterols by the Genetically Engineered Strains NwIB-X01, NwIB-X02, NwIB-X03, NwIB-X04, NwIB-X05, and NwIB-X06

Figure 5:
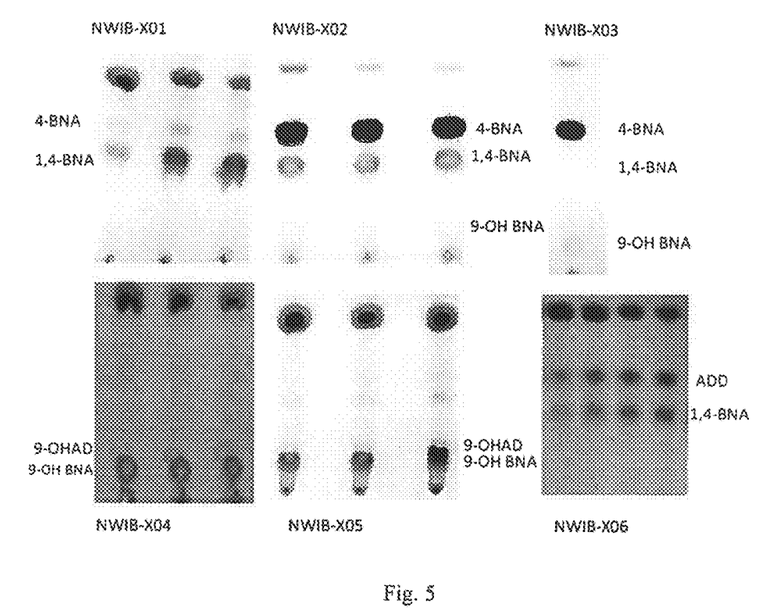
FIG. 5 is a thin layer chromatogram (TLC) of the transformation results of phytosterols by the hydroxylase coenzyme A dehydrogenase gene-deficient strain, and the acyl-coenzyme A thiolase gene-deficient strain.
Figure 6:
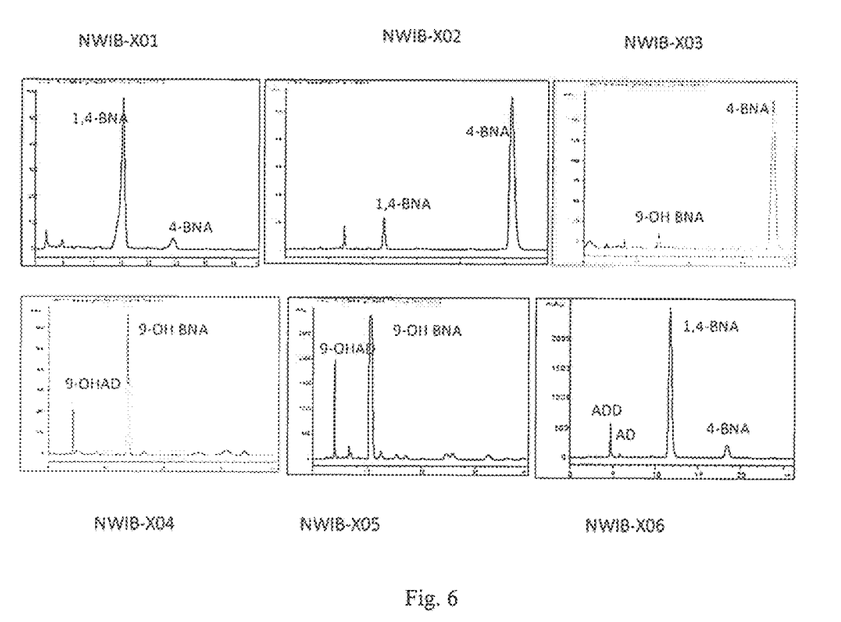
FIG. 6 is a high performance liquid chromatogram of the transformation results of phytosterols by the hydroxylase coenzyme A dehydrogenase gene-deficient strain, and the acyl-coenzyme A thiolase gene-deficient strain.

The culture conditions of the genetically engineered strain and the conditions for the transformation of the steroid can be carried out according to Example 2. In the shake flask (30 ml loaded liquid/250 ml shake flask), phytosterols are used as the substrate, and its final concentration is added to 0.5-5%, the conversion time is 5-10 days, and the results of phytosterol transformation by the engineered strains are as shown in FIG. 5 and FIG. 6.

Genetically engineered strain NwIB-X01 can transform and degrade sterol to produce 1,4-BNA and 4-BNA at the same time, wherein the product 1,4-BNA is the main product; NwIB-X02 can transform and degrade sterol and also produce 1,4-BNA and 4-BNA, wherein the product 4-BNA is the main product because of the absence of 3-ketosteroid-$\Delta^1$-dehydrogenase gene in the strain; and NwIB-X03 can transform and degrade sterol to produce 4-BNA and 9-OH-BNA, wherein the product 4-BNA is the main product as compared with NwIB-X02 because of the absence of three 3-ketosteroid-$\Delta^1$-dehydrogenase gene in the strain. Genetically engineered strain NwIB-X06 can transform and degrade sterol to produce 1,4-BNA and 4-BNA, in addition to these, it also can produce androst-4-ene-3,17-dione (AD) and androst-1,4-dien-3,17-dione (ADD).

Genetically engineered strain NwIB-X04 can transform and degrade sterol to produce 9-OH-BNA, in addition to this, it also can produce 9α-androst-4-ene-3,17-dione (9-OH-AD); and NwIB-X05 also can transform and degrade sterol to produce 9-OH-BNA.

In view of the above, according to genetically engineered mycobacterium strains of present invention constructed by the modification of hydroxyacyl-coenzyme A dehydrogenase gene and/or acyl-coenzyme A thiolase gene, they can optionally prepare 22-hydroxy-23,24-bisnorchol-1,4-dien-3-one, 22-hydroxy-23,24-bisnorchol-4-ene-3-one and 9α,22-dihydroxy-23,24-bisnorchol-4-ene-3-one compounds. These products can be used industrially in the production of adrenocorticotropic steroid drugs, and can partially substitute the current process for the production of adrenocortical hormone based on diosgenin through pregnadienolone, and thus can greatly improve the production efficiency of steroids, help to reduce the energy consumption and material consumption of steroid drug production process, simplify production steps and reduce production costs.

The aforementioned preferable embodiments are exemplary rather than limiting in nature, and many variations of the present invention are possible in light of the above teachings. It is, therefore, to be understood that all easy, equivalent variations and modifications made according to the claims and description of present invention fall into the scope of the invention as defined by the claims. The contents that have not been described in detail are the routine technical solutions.

What is claimed is:

1. A method of preparing steroidal compounds, comprising the steps of:

providing a *Mycobacterium* NwIB-00 having hydroxyacyl-coenzyme A dehydrogenase gene and acyl-coenzyme A thiolase gene, said hydroxyacyl-coenzyme A dehydrogenase gene encodes a protein having an amino acid sequence according to SEQ ID NO 2, and said acyl-coenzyme A thiolase gene encodes a protein having an amino acid sequence according to SEQ ID NO 4; and constructing six different genetically engineered *Mycobacterium neoaurum* strains NwIB-X01, NwIB-X02, NwIB-X03, NwIB-X04, NwIB-X05 and NwIB-X06 from the *Mycobacterium* NwIB-00 by the method of gene knockout, and culturing the six different genetically engineered *Mycobacterium neoaurum* strains to transform and degrade sterol to produce the steroidal compounds as follows:

NwIB-X01 lacking hydroxyacyl-coenzyme A dehydrogenase gene (hsd4A) and 3-ketosteriod-9α-hydroxylase (kshA1) produces 1,4-BNA and 4-BNA;

NwIB-X02 lacking hsd4A and 3-ketosteroid-$\Delta^1$-dehydrogenase gene (kstd1) and kshA1 produces 1,4-BNA and 4-BNA;

NwIB-X03 lacking hsd4A and kshA1 and kstd1 and kstd2 and kstd3 produces 4-BNA and 9-OH-BNA;

NwIB-X04 lacking hsd4A and kstd1 produces 9-OH-BNA and 9-OH-AD;

NwIB-X05 lacking hsd4A and kstd1 and kstd2 and kstd3 produces 9-OH-BNA; and

NwIB-X06 lacking kshA1 and acyl-coenzyme A thiolase gene (fadA5) produces 1,4-BNA and 4-BNA.

* * * * *